United States Patent [19]  [11] 4,131,747
Kurono et al.  [45] Dec. 26, 1978

[54] PROCESS FOR PREPARING α-SUBSTITUTED PHENYLALKANECARBOXYLIC ACID

[75] Inventors: Masayasu Kurono; Masaaki Toda, both of Osaka; Haruki Niwa, Kyoto; Syunji Kosuge, Takatsuji; Takahumi Iida, Nishinomiya; Kenichi Narita, Takastsuki, all of Japan

[73] Assignee: Ono Pharmaceutical Co., Ltd., Osaka, Japan

[21] Appl. No.: 743,258

[22] Filed: Nov. 19, 1976

[30] Foreign Application Priority Data
Nov. 19, 1975 [JP] Japan ................................. 50-138041

[51] Int. Cl.$^2$ ...................... C07C 63/52; C07C 63/33; C07C 65/02

[52] U.S. Cl. ................................ 562/469; 260/348.46; 260/465 D; 260/558 R; 260/559 R; 560/105; 562/459; 562/465; 562/492; 562/496

[58] Field of Search ........... 260/515 R, 515 A, 520 R, 260/521 R, 521 H

[56] References Cited
U.S. PATENT DOCUMENTS
4,042,617  8/1977  Kogure et al. ..................... 260/515 R Primary Examiner—Jane S. Myers
Attorney, Agent, or Firm—Sughrue, Rothwell, Mion, Zinn and Macpeak

[57] ABSTRACT

A process for preparing an α-substituted phenylalkanecarboxylic acid, having useful pharmaceutical properties such as analgesic, anti-inflammatory and antipyretic properties, from the corresponding ethylidenecyanoacetate by oxidation, hydrolysis, decarboxylation and oxidation.

5 Claims, No Drawings

PROCESS FOR PREPARING α-SUBSTITUTED PHENYLALKANECARBOXYLIC ACID

BACKGROUND OF THE INVENTION

This invention relates to a process for preparing an α-substituted phenylalkanecarboxylic acid having valuable pharmaceutical properties such as analgesic, anti-inflammatory and anti-pyretic properties.

SUMMARY OF THE INVENTION

More particularly, the present invention provides a process for preparing an α-substituted phenylalkanecarboxylic acid represented by the following general formula (IV):

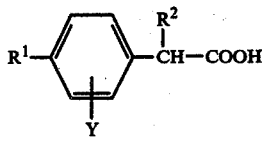

wherein $R^1$ represents a straight or branched alkyl group having 1 to 4 carbon atoms, an alkoxy group having 1 to 4 carbon atoms, a cyclohexyl group, a phenyl group, a phenoxy group or a benzyl group; $R^2$ represents a hydrogen atom or a straight or branched alkyl group having 1 to 4 carbon atoms; and Y represents a hydrogen atom or a halogen atom; which comprises the steps of: (i) treating a compound represented by the following general formula (I) and/or (I'):

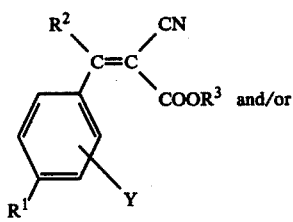

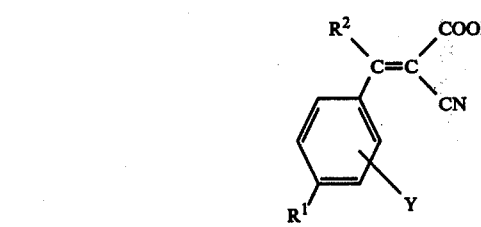

wherein $R^1$, $R^2$ and Y are the same as defined above, and $R^3$ represents a hydrogen atom, a methyl group or an ethyl group, with a peracid or a peroxide to prepare a compound represented by the following general formula (II) and/or (II'):

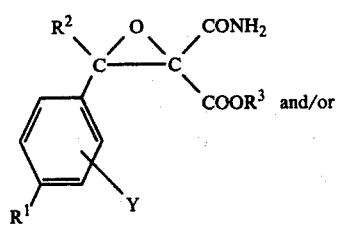

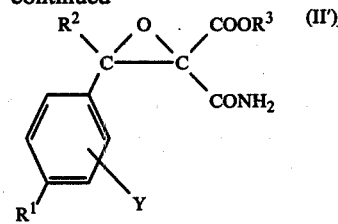

wherein $R^1$, $R^2$, $R^3$ and Y are the same as defined above; (ii) hydrolyzing the product represented by the general formula (II) and/or (II'), and then causing a decarboxylation together with a rearrangement to occur to prepare a compound represented by the following general formula (III):

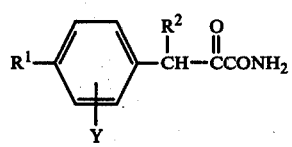

wherein $R^1$, $R^2$ and Y are the same as defined above; and (iii) oxidizing the product represented by the general formula (III) to prepare the α-substituted phenylalkanecarboxylic acid represented by the following general formula (IV):

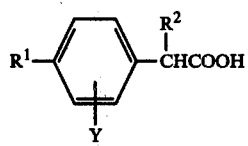

wherein $R^1$, $R^2$ and Y are the same as defined above.

DETAILED DESCRIPTION OF THE INVENTION

Examples of straight or branched alkyl groups having 1 to 4 carbon atoms for $R^1$ and $R^2$ in the general formula (IV) above include a methyl group, an ethyl group, a propyl group, an isopropyl group, a butyl group, an isobutyl group, etc.

Examples of alkoxy groups having 1 to 4 carbon atoms for $R^1$ include a methoxy group, an ethoxy group, an n-propoxy group, an isopropoxy group, an n-butoxy group, an isobutoxy group, etc.

The term "phenyl group" for $R^1$ includes both unsubstituted and substituted phenyl groups where the substituent can be a straight or branched alkyl group having 1 to 4 carbon atoms, an alkoxy group having 1 to 4 carbon atoms or a halogen atom.

The term "phenoxy group" used herein also includes both unsubstituted and substituted groups where the substituent is a halogen atom.

Examples of straight or branched alkyl groups having 1 to 4 carbon atoms for the substituted phenyl group include a methyl group, an ethyl group, a propyl group, an isopropyl group, a butyl group, an isobutyl group, etc., and examples of alkoxy groups having 1 to 4 carbon atoms as a substituent on the phenyl group include a methoxy group, an ethoxy group, an n-propoxy group, an isopropoxy group, a butoxy group, an isobutoxy group, etc.

Illustrative examples of halogen atoms for Y and for the substituted phenyl group and the substituted phenoxy group include a fluorine atom, a chlorine atom, a bromine atom and an iodine atom, with a fluorine atom and a chlorine atom being preferred.

According to the process of the present invention described above, the α-substituted phenylalkanecarboxylic acids represented by the general formula (IV) can be prepared from compounds of the general formula (I) and/or (I′) quite advantageously from an industrial standpoint and in high yield.

The compound represented by the general formula (I) and/or (I′) used as a starting material in this invention is a novel compound and can be prepared in a high yield with ease by conducting a Knoevenagel reaction between a compound represented by the general formula (V) with a compound represented by the general formula (VI) according to the procedure described in *Organic Synthesis, Collective*, Vol. 4, p. 463 (1963) or ibid., Vol. 3, p. 399 (1955).

This reaction is schematically illustrated below:

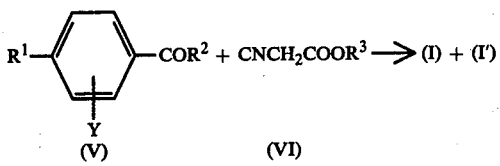

wherein R¹, R², Y and R³ are the same as defined above.

Examples of solvents which can be used include benzene, toluene, etc., and examples of catalysts which can be used include ammonium acetate, γ-aminobutyric acid, β-alanine, etc. The reaction is generally conducted at the refluxing temperature of the solvent used.

The compounds represented by the general formula (V) are described, e.g., in U.S. Pat. No. 3,755,427, British Pat. No. 1,307,284, Dutch patent application No. 6,507,505 (*Chem. Abst.*, 66 10765b), *Bull. Soc. Chim. France*, 1950, 489, *Chem. Ber.*, 38, 2491 (1905), ibid., 68, 1825 (1935), *Compt. rend.*, 133,742 (1902), *Compt. rend.*, 146, 342 (1908), *J. Amer. Chem. Soc.*, 63, 1939 (1941), ibid., 71, 3760 (1949), *J. Med. Chem.*, 15, 1297 (1972), *Rec. trav. Chim.*, 62, 713 (1943), *Teor. Eksp. Khim.*, 3, 320 (1967) *Zn. Obshch. Khim.*, 34, 977 (1964), etc. The compounds represented by the general formula (VI) are commercially available.

The present invention will be illustrated in greater detail below.

In the first step, the preparation of the compound represented by the general formula (II) and/or (II′) from the compound of the formula (I) and/or (I′) is attained by the epoxidation of the carbon-to-carbon double bond and the hydrolysis of the nitrile group to an amido group, which can be practiced by reacting various peroxides with the compound represented by the general formula (I) and/or (II) under weakly alkaline conditions in a suitable solvent.

Suitable peroxides, which can be used, for example, include hydrogen peroxide, t-butyl hydroperoxide, etc.

Examples of solvents which can be used are water, an alcohol (e.g., methyl alcohol, ethyl alcohol, etc.), a mixture of various organic solvents (e.g., methyl alcohol, ethanol, benzene, chloroform, etc.) with water, or the like. A suitable concentration of the starting material of the general formula (I) and/or (I′) is about 0.5 to about 2 M, preferably 1 to 1.5 M.

The reaction can be conducted at any temperature within the range of from about 0° C to about the boiling point of the solvent used, preferably 30° to 60° C.

The weakly alkaline conditions described above can be achieved by using sodium hydroxide, potassium hydroxide, sodium carbonate, potassium carbonate, sodium acetate, potassium acetate, sodium dihydrogen phosphate, etc., to adjust the reaction system to a pH of about 8 to about 10.

Although the theoretical amount of peroxides used is 3 mol equivalents, the peroxides are preferably employed in a slight excess amount (e.g., about 4 to about 5 mol equivalents).

The reaction is generally conducted for about 2 to about 5 hours, and the completion of the reaction can be monitored by thin-layer chromatography.

The reaction using, e.g., hydrogen peroxide as an example of a peroxide, is schematically illustrated by Reaction Scheme A below.

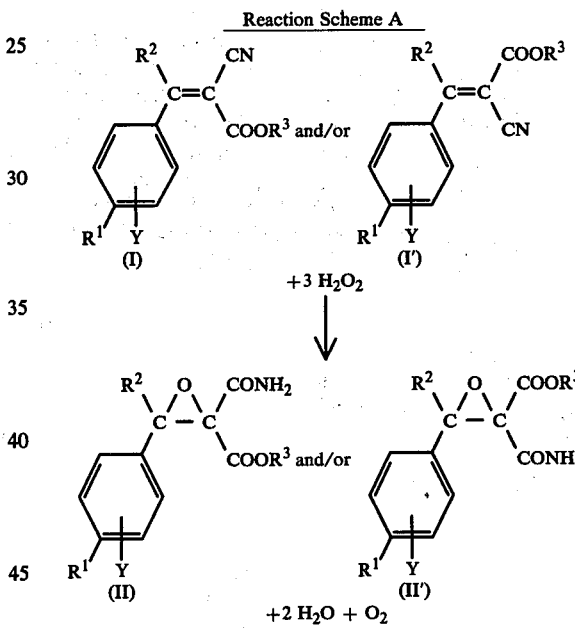

In the second step of the process of this invention, the preparation of the compound represented by the general formula (III) from the compound represented by the general formula (II) and/or (II′) is achieved by a hydrolysis of the ester group to a carboxylic acid group to convert to the compound represented by the general formula (VII) and/or (VII′), and subsequently to a decarboxylation involving a rearrangement. The conversion of the compound represented by the general formula (II) and/or (II′) to the compound represented by the general formula (III) proceeds as shown in the following Reaction Scheme B. That is, a decarboxylation reaction involving a cleavage of the epoxy group first occurs to yield a compound represented by the general formula (VII) and/or (VII′) and, via an enol body intermediate represented by the general formula (VIII), a compound represented by the general formula (III) is formed.

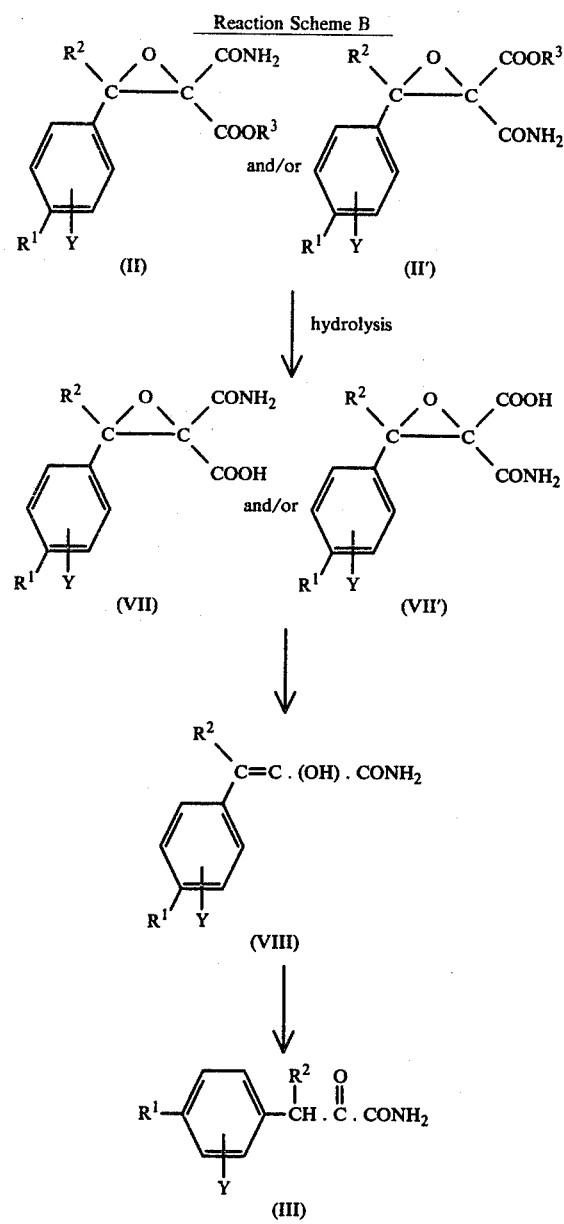

Reaction Scheme B

Hydrolysis of the compound represented by the general formula (II) and/or (II') is conducted in the presence of a solvent under alkaline conditions (e.g., a pH of above about 10). For example, water, an alcohol (e.g., methyl alcohol, ethyl alcohol, etc.), or a mixture of water or an alcohol with various organic solvents (e.g., benzene, ethyl ether, etc.) can be used as a solvent and, to achieve the alkaline conditions, an alkali such as sodium hydroxide, potassium hydroxide, sodium carbonate, potassium carbonate, or the like can be used. A suitable concentration for the compound of the general formula (II) and/or (II') is about 0.1 to about 5 M, preferably 0.5 to 2 M. The reaction can be conducted at any temperature within the range of from about 0° C to about the boiling point of the solvent used for about 30 minutes to about 2 hours. After the completion of the reaction which can be monitored using thin-layer chromatography, a mineral acid (e.g., hydrochloric acid, sulfuric acid, etc.) is added in an amount of about 1 to about 2 mol equivalents per mol equivalent of the alkali to produce the compound represented by the general formula (VII) and/or (VII').

Then, the product represented by the general formula (VII) and/or (VII') is subjected to a decarboxylation without isolation. Alternatively, the compound represented by the general formula (VII) and/or (VII') can be heated, after isolation, (e.g., by extracting with benzene or chloroform), in the presence of or absence of a suitable solvent (e.g., water, benzene, toluene, ethanol, propanol, etc.). A suitable concentration for the compound represented by the general formula (VII) and/or (VII') is about 1 to about 5 M. However, from the viewpoint of procedural simplicity, it is preferred to heat the compound represented by the general formula (VII) and/or (VII') in the solvent used for hydrolysis, without isolation, to thereby conduct the decarboxylation. The decarboxylation and rearrangement reaction is carried out at a temperature within a range of from about 70° to about 120° C, with about 80° C being preferred, for from about 30 minutes to about 2 hours until evolution of carbon dioxide ceases.

In the third step of the process of this invention, the preparation of the compound represented by the general formula (IV) from the compound represented by the general formula (III) can be conducted by oxidizing the ketoamido group to a carboxy group.

This oxidation can be achieved by oxidation with a peracid or a peroxide (e.g., hydrogen peroxide), oxidation with periodic acid or a metal oxide (e.g., potassium permanganate, etc.), oxidation with a halogen oxidant (e.g., chlorine, bromine, sodium hypochlorite, sodium hypobromite, etc.), and the like. Of these, oxidation with a halogen oxidant, in particular, a Hofmann rearrangement using an alkali metal salt of a hypohalous acid is desirable from the viewpoint of procedural ease, prevention of environmental pollution and economic cost.

Examples of alkali metal salts of hypohalous acids which can be used in the reaction include the sodium or potassium salts of hypobromous or hypochlorous acid. Suitable solvents include water or an alcohol (e.g., methyl alcohol, ethyl alcohol, etc.), although water is desirable from the point of yield and cost. At this point, benzene, chloroform, diethyl ether or a like organic solvent can be used for dissolution, if the sample is insoluble in water. The oxidation of the compound represented by the general formula (III) is carried out at a temperature from about −10° C to about room temperature (e.g., about 20°-30° C) preferably at about 0° C, for about 30 minutes to 2 hours. The oxidants are employed, preferably in a slight excess amount (e.g., about 1:1 to about 1.5 mol equivalents to the compound represented by the general formula (III). The completion of the oxidation can be determined using thin-layer chromatography and the compound represented by the general formula (IV) is recovered by filtration of the resulting precipitates after acidification of the reaction solution to a pH of about 3.

The compounds of the formula (IV) are known compounds useful as analgescis, anti-inflammatory agents and anti-pyretic agents and are described in U.S. Pat. No. 3,755,427, French Pat. No. 1,549,728 (*Chem. Absts.* 72, 12388g), *Chim. Therap.* 2, 459 (1967), *Curr. Ther. Res.* 7, 749 (1965), etc.

The present invention will now be illustrated in greater detail by reference to the following Examples and Reference Examples. However, the present invention should not in any way be construed as being limited to these Examples.

In the Examples and the Reference Examples, the abbreviations "IR" and "NMR" mean "infrared absorption" and "nuclear magnetic resonance," respectively. Further, unless otherwise indicated, all parts, percents, ratios and the like are by weight.

Reference Example 1

Preparation of Ethyl [1-(4'-Isobutylphenyl)ethylidene]cyanoacetate

In a 100 ml round-bottomed flask attached to a continuous water separator were placed 10 g (57 m mol) of 4-isobutylacetophenone, 6.57 g (58 m mol) of ethyl cyanoacetate, 658 mg (8.55 m mol) of ammonium acetate, 5.13 g (85.5 m mol) of glacial acetic acid and 20 ml of benzene. The flask was heated in an oil bath at 115° – 120° C and the water that distilled out of the mixture with the refluxing benzene was removed from the separator. After 4 hours 329 mg of ammonium acetate and 0.86 g of glacial acetic acid were added to the reaction flask and after 8 hours ammonium acetate and glacial acetic acid were again added, each in the amounts previously recited. After refluxing was continued for 12 hours, the solution was cooled and washed with two 10 ml portions of water. The reaction mixture was dried over anhydrous magnesium sulfate and the benzene was removed by distillation under reduced pressure. The residual oil was distilled under reduced pressure (0.001 mmHg). The yield of the product boiling at 125°–130°/0.001 mmHg was 14.1 g (91.6%). The product was a mixture of stereoisomers.

NMR (CCl$_4$) ppm: 0.80 – 1.00 (6H, m), 1.01 – 1.48 (3H, m), 1.65 – 2.10 (1H, m), 2.40 – 2.70 (5H, m), 3.91 – 4.40 (2H, m), 7.05 – 7.42 (4H, m).

IR CHCl$_3$ cm$^{-1}$: 2330, 2220, 1725, 1250.

Mass (m/e) : 271, 229, 228, 200, 183, 170.

REFERENCE EXAMPLE 2

Preparation of Ethyl [1-(4'-Isobutylphenyl)ethylidene]cyanoacetate

In a 100 ml round-bottomed flask attached to a continuous water separator were placed 10 g (57 m mol) of 4-isobutylacetophenone, 592 mg (11.4 m mol) of γ-aminobutyric acid, 3.26 ml of glacial acetic acid and 20 ml of benzene. The flask was heated in an oil bath at 115° – 120° C and the water that distilled out of the mixture with the refluxing benzene was removed from the separator. After 5 hours, 592 mg of γ-aminobutyric acid and 1.0 ml of glacial acetic acid were added to the reaction flask. After refluxing was continued for 20 hours, the solution was cooled and washed with two 10 ml portions of water. The reaction mixture was dried over anhydrous magnesium sulfate and the benzene was removed by distillation at reduced pressure. The residual oil was distilled under reduced pressure. The yield of the product boiling at 125° – 130°/0.001 mmHg was 14.5 g (94%). The product was a mixture of stereoisomers. The spectral data of the product were consistent with that of an authentic sample obtained in Reference Example 1.

REFERENCE EXAMPLE 3

Preparation of Ethyl [1-(4'-Biphenylyl)ethylidene]cyanoacetate

In a 200 ml round-bottomed flask attached to a continuous water separator were placed 20 g (102 m mol) of 4-phenylacetophenone, 1.18 g of ammonium acetate, 11.78 g (104 m mol) of ethyl cyanoacetate, 9.20 g of glacial acetic acid and 40 ml of benzene. The flask was heated in an oil bath at 115° to 120° C, and the water that distilled out of the mixture with the refluxing benzene was removed from the separator. After 10 hours, 590 mg of ammonium acetate and 1.54 g of glacial acetic acid were added to the reaction flask. After refluxing for 20 hours, the reaction mixture was cooled and washed with two 60 ml portions of water. The reaction mixture was dried over anhydrous magnesium sulfate and the benzene removed by distillation under reduced pressure. The residue was separated with silica gel chromatography using chloroform as a solvent. The yield of the product was 24.3 g (81.8%). The product was a mixture of stereoisomers.

NMR (CDCl$_3$) ppm: 1.03 – 1.45 (3H), 2.50 – 2.65 (3H), 3.94 – 4.40 (2H), 7.11 – 7.68 (9H).

IR (CHCl$_3$cm$^{-1}$: 2230, 1725, 1600, 1240.

Mass (m/e) : 291, 263, 262, 246, 245.

EXAMPLE 1

Preparation of 3-(4'-Isobutylphenyl)-2,3-epoxy-2-ethoxycarbonyl-butyramide (Step (1))

Into a round-bottom flask equipped with a thermometer, a dropping funnel, a stirrer and a condenser were placed 2.00 g (7.38 m mol) of ethyl [1-(4'-isobutylphenyl)ethylidene]cyanoacetate prepared as described in the Reference Examples, 1.586 g (4.43 m mol) of disodium hydrogen phosphate and 6 ml of methanol. The flask was heated in an oil bath at 55° to 60° C. To this was added dropwise 3.34 ml of 30% hydrogen peroxide with vigorous stirring over a 2 hour period. After stirring for an additional hour, the reaction mixture was cooled, poured into 5 ml of water and extracted with three 15 ml portions of benzene. The benzene layer was washed with 2 ml of 10% sodium thiosulfate and dried over anhydrous sodium sulfate. The removal of the solvent under reduced pressure afforded 1.87 g of the product (purity > 95%). The product was a mixture of stereoisomers.

NMR (CDCl$_3$) ppm: 0.79 – 1.48 (9H, m), 1.60 – 2.10 (4H, m), 2.44 (2H, broad d, J = 7.0 Hz), 3.70 – 4.50 (2H, m), 5.80 – 7.00 (2H), 7.01 – 7.40 (4H).

IR (CHCl$_3$) cm$^{-1}$: 3525, 3400, 1745, 1700, 1575.

Mass (m/e) : 305, 260, 118.

Preparation of 3-(4'-Isobutylphenyl)-2-oxobutyramide (Step (2))

To a two-necked flask equipped with a stirrer and a dropping funnel was added a solution of 3.84 g (12.59 m mol) of 3-(4'-isobutylphenyl)-2,3-epoxy-2-ethoxycarbonylbutyramide prepared as in (1) above in 8 ml of methanol, and then 4.72 ml of 4.00 N methanolic potassium hydroxide was added dropwise with stirring at 20° – 30° C. The mixture was stirred for 30 minutes at room temperature. After removal of methanol under reduced pressure, the residue was poured into 20 ml of water and washed with two 20 ml portions of benzene. The aqueous layer was acidified with 9.45 ml of 2 N hydrochloric acid, and then heated at 110° C in an oil bath for 20 minutes and cooled to room temperature. The resulting precipitate was collected by filtration and dried. The yield of the product was 2.68 g (91.5%), which on recrystallization from benzene/n-hexane (1:1 by volume) gave 2.45 g of colorless crystals, m.p. 112° –113° C.

NMR (CDCl$_3$) ppm: 0.88 (6H, d, J = 6.5 Hz), 1.41 (3H, d, J = 7.0 Hz), 1.60 - 2.10 (1H, m), 2.42 (2H, d, J = 7.5 Hz), 4.79 (1H, q, J = 7.0 Hz), 6.30 - 6.90 (1H, broad), 6.98 - 7.20 (4H, m).

IR (KBr) cm$^{-1}$: 3450, 3230, 1730, 1675, 1500.

Mass (m/e): 233, 188, 161, 145.

Preparation of 2-(4'-Isobutylphenyl)propionic Acid (Step (3))

To a three-necked flask equipped with a stirrer, a dropping funnel and a thermometer were placed 4.46 ml of 0.5 N sodium hydroxide and a solution of 1.00 g (4.29 m mol) of 3-(4'-isobutylphenyl)-2-oxobutyramide prepared as in (2) above in 4.0 ml of chloroform under cooling in an ice-salt bath. To the cold solution was added slowly with thorough mixing 892 mg (5.58 m mol) of bromine while maintaining the temperature at 0° - 2° C. The resulting solution was stirred for an additional hour at 0° C, and then washed with benzene to remove the neutral products. To the aqueous layer was added 134 mg of sodium sulfite to destroy the excess sodium hypobromite, and further 1.8 ml of conc. hydrochloric acid (about 12 N) was added. The acidic aqueous solution was extracted with benzene. The benzene layer was washed with water, dried over anhydrous sodium sulfate and concentrated under reduced pressure to give 735 mg (83%) of white crystals, which on recrystallization from n-hexane afforded colorless crystals, m.p. 74.5° -76.0° C.

NMR (CDCl$_3$) ppm: 0.89 (6H, d, J = 6 Hz), 1.49 (3H, d, J = 7 Hz), 1.65 - 2.00 (1H, m), 2.43 (2H, d. J = 7 Hz), 3.69 (1H, q, J = 7Hz), 7.00 - 7.30 (4H, m), 9.60 (—COOH).

IR (KBr) cm$^{-1}$: 1710, 1420, 1320, 1270, 1230, 1180, 940, 780.

Mass (m/e): 206, 163, 161, 149.

EXAMPLE 2

Preparation of 3-(4'-Isobutylphenyl)-2-oxobutyramide (Steps (1) and (2) without isolation)

Into a round-bottom flask equipped with a thermometer, a dropping funnel, a stirrer and a condenser were placed 10.0 g (36.9 m mol) of ethyl [1-(4'-isobutylphenyl)ethylidene]cyanoacetate, prepared as described in the Reference Examples, 7.93 g (22.1 m mol) of disodium hydrogen phosphate and 30 ml of methanol. The flask was heated in an oil bath to 55° - 60° C. To this was added dropwise 16.7 ml (14.8 m mol) of 30% hydrogen peroxide with vigorous stirring over a 2 hour period. After the stirring had been continued for an additional hour, the reaction mixture was cooled to room temperature (about 20° - 30° C). To this was added slowly in a dropwise manner 13.8 ml (55.2 m mol) of 4.0 N methanolic potassium hydroxide with stirring at room temperature. After an additional hour with stirring, the reaction mixture was poured into 30 ml of water and washed with three 30 ml portions of benzene. The aqueous solution was placed in a round-bottom flask equipped with a condenser and a dropping funnel and heated in an oil bath (80° C). To this was added dropwise 27.6 ml (55.2 m mol) of 2 N hydrochloric acid over a 20 minute period. After the heating had been continued for 30 minutes with stirring, the solution was cooled slowly to 0° C. The resulting precipitate was collected by filtration and dried under reduced pressure. The yield was 7.8 g (90.7%), and the product obtained was then washed with two 10 ml portions of n-hexane to afford 6.69 g (77.8%) of colorless crystals, m.p. 112° -113° C. The spectral data of the product were consistent with that of an authentic sample obtained in Example 1, Step (2).

Preparation of 2-(4'-Isobutylphenyl)propionic Acid (Step (3))

In a three-necked flask equipped with a thermometer, a dropping funnel and screw type stirrer was placed 98.0 ml (196 m mol) of 2 N sodium hydroxide under cooling in an ice-salt bath to about −5° to about 0° C. To the cold solution were added slowly with thorough mixing 2.52 ml (49.0 m mol) of bromine while maintaining the temperature at −5° - 0° C over about a 5 minute period. After vigorous stirring for 10 minutes at −4° C to 0° C, the reaction mixture was warmed slowly to 70° C over a 1.5 hour period, and then cooled to room temperature and washed with 35 ml of benzene to remove the neutral products. To the aqueous layer was added 1.17 g (11.32 m mol) of sodium sulfite, and further conc. hydrochloric acid to a pH of about 2. After stirring in an ice-bath for 1 hour, the resulting precipitate was collected by filtration and dried under reduced pressure. The yield was 7.85 g, which on recrystallization from n-hexane (15 ml) gave 7.38 g (95.0%) of colorless crystals. The spectral data of the product were consistent with that of an authentic sample obtained in Example 1.

EXAMPLE 3

Preparation of 3-(4'-Biphenylyl)-2,3-epoxy-2-ethoxycarbonylbutryamide (Step (1))

Into a round-bottom flask equipped with a thermometer, a dropping funnel and a condenser were placed 7.726 g (26.5 m mol) of ethyl [1-(4'-biphenylyl)ethylidene]cyanoacetate prepared as described in the Reference Examples, 5.695 g (15.9 m mol) of disodium hydrogen phosphate and 23 ml of methanol. The flask was heated in an oil bath at 55° - 60° C. To this was added dropwise 12.0 ml of 30% hydrogen peroxide with vigorous stirring over a 3 hour period. After stirring for an additional hour, the reaction mixture was cooled to room temperature (about 20° to 30° C) and poured into 10 ml of water, and then extracted three times with benzene. The benzene layer was washed with 2.5 ml of 10% sodium thiosulfate and dried over anhydrous magnesium sulfate. The removal of the solvent under reduced pressure afforded an oil which was chromatographed on silica gel using benzene/ethyl acetate (3:1 by volume) as a solvent to obtain 7.36 g of product (85.5%). The product was a mixture of stereo-isomers.

NMR (CDCl$_3$) ppm: 0.75 - 1.45 (3H), 1.70 - 1.84 (3H), 4.26 - 4.50 (2H), 7.23 - 7.64 (9H).

IR (KBr) cm$^{-1}$: 1740, 1680, 1600, 1250.

Mass (m/e): 325, 281, 252, 209.

Preparation of 3-(4'-Biphenylyl)-2-oxobutyramide (Step (2))

To a two-necked flask equipped with a stirrer, and a dropping funnel was added a solution of 4.43 g (13.7 m mol) of 3-(4'-biphenylyl)-2,3-epoxy-2-ethoxycarbonylbutyramide, produced as described in (1) above, in 9 ml of methanol, and then 5.1 ml (20.5 m mol) of 4.05 N methanolic potassium hydroxide was added dropwise with stirring at room temperature. The mixture was stirred for 30 minutes and the resulting precipitate was collected by filtration and dried under reduced pressure with the potassium salt being obtained. The yield of the potassium salt was 3.85 g. The solution of the potassium salt in 33 ml of water was poured into a round-bottom flask equipped with a condenser and a dropping funnel, and heated at 100° C in an oil bath with stirring. To this was added dropwise 5.75 ml (11.5 m mol) of 2 N hydrochloric acid over about a 20 minute period. After heating at 100° C for 30 minutes with stirring, the solution was cooled to room temperature. The resulting precipitate was collected by filtration and dried under reduced pressure, which on recrystallization from methanol gave 2.76 g of colorless crystals (77.4%), m.p. 200° - 201° C.

NMR (DMSO-$d_6$) ppm: 1.37 (3H, d, J = 7.0 Hz), 4.78 (1H, q, J = 7.0 Hz), 7.23 - 8.10 (11H).

IR (KBr) cm$^{-1}$: 3420, 1725, 1665, 1485, 1405.

Mass (m/e): 253, 208, 181, 165, 152.

Preparation of 2-(4'-Biphenylyl)propionic Acid (Step (3))

To a three-necked flask equipped with a stirrer, a dropping funnel and a thermometer was placed 41.1 ml (20.5 m mol) of 0.5 N sodium hydroxide, and then 0.24 ml (4.74 m mol) of bromine was added dropwise with vigorous stirring over about a 5 minute period in an ice-salt bath at −10° to 5° C. To this was added a solution of 1.00 g (3.95 m mol) of 3-(4'-biphenylyl)2-oxobutyramide, prepared as described in (2) above, in 24 ml of chloroform slowly at a temperature of below 0° C. After vigorous stirring for 30 minutes at −5° to 0° C, the reaction mixture was warmed slowly to 60° C over a 2.5 hour period, and then cooled to room temperature. To this was added 82 mg (0.79 m mol) of sodium sulfite with stirring, and then the chloroform layer was separated. The aqueous layer was washed with a 10 ml portion of chloroform, acidified with conc. hydrochloric acid (about 12N) to a pH of about 3 and extracted with three 20 ml portions of chloroform. After drying over anhydrous magnesium sulfate, removal of the chloroform yielded 850 mg of crystals, which on recrystallization from methanol afforded 813 mg (91.0%) of colorless crystals, m.p. 147° - 148° C.

NMR (CDCl$_3$) ppm: 1.55 (3H, d, J = 7.0 Hz), 3.78 (1H, q, J = 7.0 Hz), 7.20 - 7.73 (9H), 9.00 - 9.50 (1H).

IR (KBr) cm$^{-1}$: 3000, 1700, 1610, 1480, 1230.

Mass (m/e): 226, 182, 165, 151.

While the invention has been described in detail and with reference to specific embodiments thereof, it will be apparent to one skilled in the art that various changes and modifications can be made therein without departing from the spirit and scope thereof.

What is claimed is:

1. A process for preparing an α-substituted phenylalkanecarboxylic acid represented by the following general formula (IV)

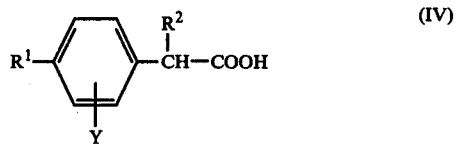
(IV)

wherein $R^1$ represents a straight or branched alkyl group having 1 to 4 carbon atoms, a straight or branched alkoxy group having 1 to 4 carbon atoms, a cyclohexyl group, an unsubstituted phenyl group or a phenyl group substituted with a straight or branched alkyl group having 1 to 4 carbon atoms, a straight or branched alkoxy group having 1 to 4 carbon atoms or a halogen atom, an unsubstituted phenoxy group or a phenoxy group substituted with a halogen atom, or a benzyl group; $R^2$ represents a hydrogen atom or a straight or branched alkyl group having 1 to 4 carbon atoms; and Y represents a hydrogen atom or a halogen atom; which comprises:

(i) treating a compound represented by the following general formula (I) and/or (I'):

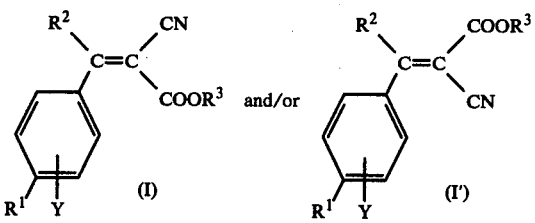

wherein $R^1$, $R^2$ and Y are the same as defined above; and $R^3$ represents a hydrogen atom or an alkyl group; with a peroxide in the presence of a solvent at a temperature ranging from about 0° C to about the boiling point of the solvent and under weakly alkaline conditions of a pH of about 8 to about 10 and using about 3 to about 5 molar equivalents of said peroxide to the total of said compound of the general formula (I) and/or (I') to prepare a compound represented by the following general formula (II) and/or (II'):

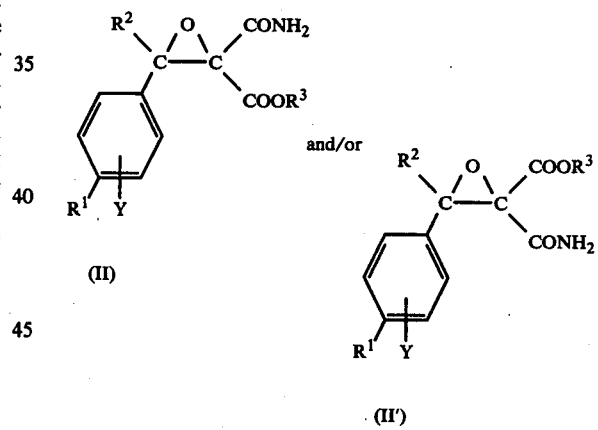

wherein $R^1$, $R^2$, $R^3$ and Y are the same as defined above;

(ii) hydrolyzing the compound represented by the general formula (II) and/or (II') ) wherein said hydrolysis is in the presence of a solvent under alkaline conditions at a temperature of from about 0° C to about the boiling point of the solvent, and then causing a decarboxylation by heating to a temperature of about 70° to about 120° C involving a rearrangement to produce a compound represented by the following general formula (III):

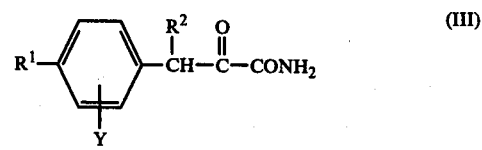
(III)

wherein $R^1$, $R^2$, and Y are the same as defined above; and (iii) oxidizing the compound represented by the general formula (III) in the presence of a solvent and at a temperature of about $-10°$ C to about room temperature with an oxidant employed in an amount of about 1.1 to about 1.5 mol equivalents to said compound represented by the general formula (III) to obtain the compound represented by the general formula (IV).

2. The process of claim 1, wherein said alkyl group for $R^1$ and $R^2$ is a methyl group, an ethyl group, a propyl group, an isopropyl group, a butyl group or an isobutyl group; wherein said alkoxy group for $R^1$ is a methoxy group, an ethoxy group, an n-propoxy group, an isopropoxy group, an n-butoxy group or an isobutoxy group, and wherein said halogen atom for Y and as said substituent is a fluorine atom, a chlorine atom, a bromine atom or an iodine atom.

3. The process of claim 1, wherein said peroxide is hydrogen peroxide or t-butyl hydroperoxide.

4. The process of claim 1, wherein said oxidizing in step (iii) is oxidizing with a peracid or a peroxide, oxidizing with periodic acid or a metal oxide or oxidizing with a halogen oxidant.

5. The process of claim 1, wherein said oxidizing in step (iii) is using an alkali metal salt of a hypohalous acid.

* * * * *